United States Patent
Janik

(10) Patent No.: US 12,178,944 B2
(45) Date of Patent: Dec. 31, 2024

(54) OPTICAL SENSOR FOR DETERMINING A DIALYSIS DOSE

(71) Applicant: B. Braun Avitum AG, Melsungen (DE)

(72) Inventor: Waldemar Janik, Melsungen (DE)

(73) Assignee: B. Braun Avitum AG, Melsungen (DE)

( * ) Notice: Subject to any disclaimer, the term of this patent is extended or adjusted under 35 U.S.C. 154(b) by 0 days.

(21) Appl. No.: 18/564,074

(22) PCT Filed: May 25, 2022

(86) PCT No.: PCT/EP2022/064245
§ 371 (c)(1),
(2) Date: Nov. 25, 2023

(87) PCT Pub. No.: WO2022/248571
PCT Pub. Date: Dec. 1, 2022

(65) Prior Publication Data
US 2024/0269359 A1    Aug. 15, 2024

(30) Foreign Application Priority Data

May 26, 2021   (DE) .................. 10 2021 113 519.2

(51) Int. Cl.
*A61M 1/16* (2006.01)
(52) U.S. Cl.
CPC .............. *A61M 1/1609* (2014.02); *A61M 2202/0498* (2013.01); *A61M 2205/3306* (2013.01)
(58) Field of Classification Search
None
See application file for complete search history.

(56) References Cited

U.S. PATENT DOCUMENTS

| 8,834,720 B2 | 9/2014 | Ahrens |
| 2011/0309019 A1 | 12/2011 | Ahrens |
| (Continued) | | |

FOREIGN PATENT DOCUMENTS

| CN | 102325555 A | 1/2012 |
| CN | 102946919 A | 2/2013 |
| (Continued) | | |

OTHER PUBLICATIONS

Uhlin et al, "Dialysis dose (Kt/V) and clearance variation sensitivity using measurement of ultraviolet-absorbance (on-line), blood urea, dialysate urea and ionic dialysance", Nephrol Dial Transplant (2006) 21: 2225-2231 (Year: 2006).*

(Continued)

*Primary Examiner* — Krishnan S Menon
(74) *Attorney, Agent, or Firm* — Christopher A. Rothe; CM Law

(57) ABSTRACT

A device for determining a dialysis efficiency/dialysis dose of an extracorporeal blood treatment process has a radiation source, a cuvette, a detection unit and a control unit. The radiation source emits radiation, the intensity of which is controlled by adjusting a current intensity applied to the radiation source. The cuvette is preferably provided with an inlet and outlet, and is penetrated by radiation emitted by the radiation source. The detection unit detects the intensity of the radiation after the radiation passes the cuvette. The control unit determines the dialysis efficiency/dialysis dose from the intensity detected by the detection unit. The control unit, which is connected to the radiation source and detection unit, reduces the intensity of the radiation by adjusting the current intensity during the extracorporeal blood treatment process at least once, based on a drop in concentration of substances excreted in the urine in the dialysis fluid.

12 Claims, 6 Drawing Sheets

(56) References Cited

U.S. PATENT DOCUMENTS

| | | | |
|---|---|---|---|
| 2013/0105371 A1 | 5/2013 | Frorip et al. | |
| 2013/0153474 A1 | 6/2013 | Frorip et al. | |
| 2013/0237896 A1 | 9/2013 | Meibaum et al. | |
| 2014/0046150 A1* | 2/2014 | Gagel .................... | A61M 1/16 600/317 |
| 2014/0098359 A1 | 4/2014 | Gross et al. | |
| 2016/0045657 A1 | 2/2016 | Krause et al. | |

FOREIGN PATENT DOCUMENTS

| | | |
|---|---|---|
| CN | 105363082 A | 3/2016 |
| DE | 102011008482 A1 | 1/2012 |
| EP | 1083948 B1 | 3/2004 |
| EP | 2163271 A1 | 3/2010 |
| EP | 2397167 A1 | 12/2011 |
| JP | 2015070065 A | 4/2015 |
| WO | 2013186357 A1 | 12/2013 |

OTHER PUBLICATIONS

Written Opinion received in International Application No. PCT/EP2022/064245 dated Sep. 28, 2022, with translation, 12 pages.
Office Action received in European Application No. 22 731 527.2-1113 dated Nov. 22, 2023, with translation, 14 pages.
Search Report received in German Application No. 10 2021 113 519.2 dated Feb. 7, 2022, with translation, 10 pages.
Search Report received in International Application No. PCT/EP2022/064245 dated Sep. 28, 2022, with translation, 5 pages.
Uhlin F., et al., "Estimation of Delivered Dialysis Dose by On-line Monitoring of the Ultraviolet Absorbance in the Spent Dialysate", Am J Kidney Dis. Vol 41, No. 5 (May 2003, pp. 1026-1036.
Office Action received in Chinese Application No. 202280037860.5 dated Apr. 12, 2024, with translation, 8 pages.
Office Action received in Japanese Application No. 2023-572980 dated Apr. 16, 2024, with translation, 2 pages.

* cited by examiner

OPTICAL SENSOR FOR DETERMINING A DIALYSIS DOSE

CROSS-REFERENCE TO RELATED APPLICATION(S)

This application is the United States national phase entry of International Application No. PCT/EP2022/064245, filed on May 25, 2022, and claims priority to German Application No. 10 2021 113 519.2, filed on May 26, 2021. The content of International Application No. PCT/EP2022/064245 and German Application No. 10 2021 113 519.2 are incorporated by reference herein in their entireties.

FIELD

The present disclosure relates to an optical measuring device for non-invasively determining a dialysis dose.

BACKGROUND

The Kt/V value is used as a parameter to assess the efficiency of extracorporeal blood treatment, such as hemodialysis. K stands for the clearance, t for the therapy duration and V for the patient-specific distribution volume of urea in the body.

Various models can be used to determine the Kt/V value. The simplest formula for determining the Kt/V value during dialysis therapy takes into account neither the generation of urea in the patient during therapy nor the so-called rebound effect. In order to determine the Kt/V value in this case, the rule:

$$\frac{Kt}{V} = \ln\left(\frac{c_0}{c(t)}\right)$$

is used. $c_0$ stands for the initial urea concentration and $c(t)$ for the urea concentration at a given time t.

The most commonly used model is the single-pool model, which takes into account the urea generation during therapy/the temporal course of the extracorporeal blood treatment. A simplified assumption is made that urea is only dissolved in a large distribution volume.

In comparison to the model above, it is taken into account that urea is produced in the patient's body during therapy. Furthermore, the model takes into account that convection caused by ultrafiltration also removes urea. In order to determine the Kt/V value in this case, the rule:

$$sp\frac{Kt}{V} = -\ln\left(-0.008 \times t + \frac{c(t)}{c_0}\right) + \left(4 - 3.5 \times \frac{c(t)}{c_0}\right) \times \frac{UF}{W}$$

is used. UF stands for the ultrafiltration volume and W for the weight of the patient.

There is also a model that takes the rebound effect into account. In reality, the movement of urea through the body is not possible without restrictions, since urea is present in the intracellular, extracellular and intravascular space. The model, which deviates from the single-pool model and takes into account the existence of these different spaces, allows a so-called equilibrated Kt/V to be determined. The backflow of urea after therapy from organs with low blood flow into the intravascular space is thus taken into account.

There are substantially three methods for technically measuring the value. By taking patient blood before and after blood treatment and determining the urea concentration in the laboratory, the Kt/V value can then be calculated. However, this method is associated with high costs for laboratory and personnel expenses as well as consumables and only provides a Kt/V value retrospectively, making it impractical for daily routine.

The second option involves briefly changing the composition of the dialysis fluid during the course of a treatment. By measuring the conductivity of the dialysis fluid upstream and downstream of the dialyzer before and during the change in conductivity, the dialysance can then be calculated. This makes use of the fact that the sodium ion, which contributes significantly to conductivity, has similar diffusion properties to the urea molecule. The advantages of this method are that no additional costs are incurred and almost continuous measurement is possible during each therapy. The disadvantage, however, is that the change in the composition of the dialysis fluid firstly requires a certain amount of time, so that a completely continuous measurement is not possible, and secondly may lead to an undesirable distortion of the sodium balance during dialysis.

A much more elegant way of Kt/V determining is described in 'Estimation of delivered dialysis dose by online monitoring of the ultraviolet absorbance in the spent dialysate, Uhlin, F.; Lindberg, LG.; Magnusson M. Am J Kidney Dis. 2003 May; 41 (5): 1026-36'. The absorbance is determined at the dialysis fluid outlet and the Kt/V value is calculated from this. A measuring device based on this is the Adimeasensor.

EP2163271 describes a method for determining a Kt/V value. Here, the absorption of the used dialysis fluid is measured via a UV sensor. The determined absorption is then evaluated and output by a computer. A constantly high current intensity is applied to the UV radiation source. This leads to self-heating of the UV radiation source, which can result in fluctuations in the intensity of the radiation emitted by the radiation source. In addition, a high current intensity leads to ageing of the UV radiation source and thus to a reduction in the service life of the UV radiation source.

Other methods for determining the Kt/V value are based, for example, on determining the conductivity of the dialysis fluid, as described above. For this purpose, it may be necessary to briefly change the composition of the dialysis fluid, the blood flow rate or the dialysis fluid flow rate in order to determine the current dialysis dose.

SUMMARY

The object of the invention is therefore to avoid or at least reduce the disadvantages of the prior art. In particular, a dialysis efficiency/dialysis dose of an extracorporeal blood treatment is to be determined via a radiation source, in particular via a UV radiation source, and a detection unit, wherein the service life of the radiation source is to be extended and the power consumption of the radiation source is to be reduced.

This object is solved by the device according to the invention for determining a dialysis dose of an extracorporeal blood treatment.

The device for determining a dialysis efficiency/dialysis dose of an extracorporeal blood treatment comprises a radiation source, a cuvette, at least one detection unit and a regulation/control unit.

The radiation source is provided and configured to emit radiation, the intensity of which is controlled/regulated by adjusting the current intensity applied to the radiation source.

The cuvette is preferably equipped with a dialysis fluid inlet and a dialysis fluid outlet and is provided and configured to be penetrated by the radiation emitted by the radiation source.

The detection unit is provided and configured to detect the intensity of the radiation after it has passed through the cuvette as a measuring detector.

The regulation/control unit determines the dialysis efficiency/dialysis dose from the intensity of the radiation detected by the detection unit. In addition, the regulation/control unit is connected to the radiation source and the detection unit and is provided and configured to reduce the intensity of the emitted radiation by adjusting the current intensity at least once over the temporal course of the extracorporeal blood treatment, based on a decrease in a concentration of substances usually excreted in the urine in the dialysis fluid.

In other words, the device for determining the dialysis efficiency of an extracorporeal blood treatment has a radiation source, in particular a UV radiation source, which emits radiation, in particular light, with a wavelength in the ultraviolet range. The wavelength of the emitted radiation is preferably in the range from 100 nm to 380 nm, particularly preferably in the range from 250 nm to 300 nm and for example at 254 nm or 280 nm. The intensity of the radiation emitted by the radiation source is controlled via the current intensity with/to which the radiation source is operated/subjected. For example, the intensity of the emitted radiation can be increased by increasing the current intensity and the intensity of the emitted radiation can be reduced by reducing the current intensity.

The cuvette is preferably provided and constructed as a tubular flow cell. Dialysis fluid flows into the cuvette via a dialysis fluid inlet. The dialysis fluid leaves the cuvette through a dialysis fluid outlet provided downstream of the dialysis fluid inlet in the direction of flow of the dialysis fluid. Preferably, both the dialysis fluid inlet and the dialysis fluid outlet are provided and configured to be connected to a tube or a line. The cuvette is penetrated by the radiation emitted by the radiation source and is made of plastic, glass or quartz glass, for example.

The detection unit is preferably a photodetector and is provided and configured to detect the radiation emitted by the radiation source. In other words, the detection unit is configured to detect the intensity of radiation having the wavelength of the radiation emitted by the radiation source. In a preferred embodiment, the detection unit converts the radiation into an electrical signal using the photoelectric effect. In a further preferred embodiment, an electrical resistance changes depending on the intensity of the incident radiation.

The regulation/control unit receives the determined intensity of the detected radiation from the detection unit, preferably in the form of an electrical signal. The regulation/control unit uses this intensity value of the radiation to determine the dialysis efficiency/dialysis dose. The regulation/control unit controls the intensity of the emitted radiation of the radiation source by adjusting the current intensity during the temporal course of the extracorporeal blood treatment, wherein the current intensity and thus the intensity of the emitted radiation is reduced at least once during the temporal course of the extracorporeal blood treatment. This reduction of the emitted radiation is based on the decrease of the concentration of substances usually excreted in the urine in the dialysis fluid. The magnitude of the decrease in the concentration of substances usually excreted in the urine in the dialysis fluid is measured in a first preferred embodiment. In a further preferred embodiment, the magnitude of the decrease of the substances usually excreted in the urine in the dialysis fluid is predicted over the temporal course of the extracorporeal blood treatment.

In still other words, the core of the invention is that the intensity of the radiation emitted by the radiation source is reduced at least once over the temporal course of the extracorporeal blood treatment, this reduction being based on the reduction in the concentration of substances usually excreted in the urine in the dialysis fluid.

Reducing the intensity of the emitted radiation in this way means that the radiation source is subjected to less stress over the temporal course of the extracorporeal blood treatment, thereby extending the service life of the radiation source. In addition, the power consumption of the radiation source can be reduced.

When determining the dialysis dose, there is also no contact with the dialysate or the patient's blood, which facilitates handling and prevents contamination.

A further advantage of the measurement method is that the composition of the dialysis fluid, the blood flow rate or the dialysis fluid flow rate does not have to be changed to determine the dialysis dose, making it a passive measurement method.

Furthermore, the use of a detection unit with a larger linear measuring range is possible, which enables the measurement of higher absorbance values and thus more accurate Kt/V values can be determined.

In one aspect of the device, the regulation/control unit is provided and configured to control the radiation source in such a way that the intensity of the radiation detected by the detection unit remains constant over the temporal course of the extracorporeal blood treatment.

In other words, the current intensity applied to the radiation source is controlled by the regulation/control unit in such a way that, after an adjustment phase, the intensity of the radiation is kept constant over the temporal course of the extracorporeal blood treatment detected at the detection unit.

As the concentration of radiation-absorbing substances usually excreted in the urine in the used dialysis fluid decreases over the temporal course of the extracorporeal blood treatment and thus less of the radiation emitted through the cuvette by the radiation source is absorbed by the substances usually excreted in the urine, the regulation/control unit reduces the current intensity and thus the intensity of the emitted radiation over the temporal course of the extracorporeal blood treatment in order to keep the intensity of the radiation detected by the detection unit constant.

Such control can preferably be implemented using PI or PID controllers. The detected intensity of the radiation at the detection unit at the time after the adjusting phase (I(t3)) is the reference input variable, the detected intensity of the radiation (I(t)) at the detection unit is the process variable and the current/the current intensity is the controlled variable.

In another aspect of the device, the current intensity applied to the radiation source is evaluated/used to determine the dialysis efficiency/dialysis dose.

In other words, the current intensity applied to the radiation source over the temporal course of the extracorporeal blood treatment is preferably evaluated by the regulation/control unit in order to determine the dialysis efficiency/dialysis dose.

In a further aspect of the device, the dialysis efficiency/dialysis dose is the Kt/V value, where K describes the clearance, t the therapy duration and V the patient-specific distribution volume of urea in the body. The regulation/control unit is provided and configured to determine the dialysis efficiency/dialysis dose using the rule Kt/V=ln(I(t3)/I(t)), where I describes the current intensity, t3 a fixed time and t the therapy duration/time.

In other words, the Kt/V value is determined via the rule $$\frac{Kt}{V} = \ln\left(\frac{I(t3)}{I(t)}\right)$$

preferably determined in the regulation/control unit, with K as clearance, t as therapy duration and V as patient-specific distribution volume of urea in the patient's body. The detected intensity of the radiation at the detection unit at the time after the adjusting phase is detected in the form of a current intensity and designated as I(t3) and the detected intensity of the radiation at the detection unit is also detected in the form of a current intensity and designated as I(t).

In a further aspect of the device, the dialysis efficiency/dialysis dose is the Kt/V value, where K describes the clearance, t the therapy duration and V the patient-specific distribution volume of urea in the body. The regulation/control unit is provided and configured to determine the dialysis efficiency/dialysis dose using the rule Kt/V=−ln(−0.008*t+(I(t)/I(t3))+(4−3.5*(I8t)/I(t3))*UF/W, where I describes the current intensity, t3 a fixed time, t the therapy duration, UF the ultrafiltration volume and W the weight of the patient.

In other words, the Kt/V value is determined via the rule $$sp\frac{Kt}{V} = -\ln\left(-0.008 \times t + \frac{I(t)}{I(t3)}\right) + \left(4 - 3.5 \times \frac{I(t)}{I(t3)}\right) \times \frac{UF}{W}$$

preferably determined in the regulation/control unit, with K as clearance, t as therapy duration and V as patient-specific distribution volume of urea in the patient's body. The detected intensity of the radiation at the detection unit at the time after the adjusting phase is detected in the form of a current intensity and designated as I(t3) and the detected intensity of the radiation is also detected in the form of a current intensity and designated as I(t). Furthermore, UF describes the ultrafiltration volume and W the weight of the patient.

In a further aspect of the device, the determined current intensity is normalized to a reference temperature.

In other words, the current intensity applied to the radiation source and evaluated by the regulation/control unit to determine the dialysis efficiency/dialysis dose is normalized to a reference temperature before evaluation. This is done because the intensity of the radiation emitted by the radiation source is temperature-dependent. As the temperature increases, the intensity of the emitted radiation decreases at constant current/constant current intensity. Preferably, the dialysis fluid temperature is detected at a temperature sensor at the dialysis fluid outlet of the dialysis machine.

Preferably, the current is compensated to the reference temperature of 37° C. This is done particularly preferably via the rule $$I_{37° C.} = I_T - \alpha \times (T - 37° C.)$$

where $I_{37° C.}$ stands for the current compensated to 37° C., $I_T$ for the current detected at the measured temperature T and α describes a temperature coefficient.

In addition to compensation to 37° C., compensation to any other temperature is also possible.

In a further aspect, the device has a further detection unit which is provided and configured to detect the intensity of the radiation emitted by the radiation source as a reference detection unit. The course of therapy comprises at least one adjusting phase and at least one measuring phase, wherein the regulation/control unit reduces the intensity of the emitted radiation over the temporal course of the extracorporeal blood treatment at least once in the adjusting phase, and the regulation/control unit controls the radiation source by adjusting the current intensity in such a way that the intensity of the radiation detected by the reference detection unit remains constant during the measuring phase and the intensity of the radiation is evaluated at the measuring detection unit to determine the dialysis efficiency/dialysis dose during the measuring phase.

In other words, in addition to the detection unit provided and configured as a measuring detection unit, a further detection unit provided and configured as a reference detection unit is provided in the device. This reference detection unit is used to compensate for possible fluctuations in the intensity of the radiation emitted by the radiation source. Preferably, the radiation emitted by the radiation source is divided at a radiation divider provided in front of the cuvette in the direction of radiation, so that a first part of the radiation passes through the cuvette and is detected by the measuring detection unit and a second part of the radiation is detected by the reference detection unit without passing through the cuvette. Alternatively, the reference detection unit is mounted and positioned in such a way that it can directly detect the radiation emitted by the radiation source without the radiation passing through the cuvette. In this case, the radiation divider can be omitted.

The course of therapy is divided into at least one adjusting phase and at least one measuring phase. The regulation/control unit is provided and configured to reduce the intensity of the radiation emitted by the radiation source at least once in the adjusting phase. In addition, the regulation/control unit is provided and configured to control the radiation source by adjusting the current intensity applied to the radiation source in such a way that the radiation detected by the reference detection unit remains constant during the measuring phase. The regulation/control unit is further provided and configured to use the intensity of the radiation detected by the measuring detection unit during the measuring phase to determine the dialysis efficiency/dialysis dose.

In a further aspect of the device, the adjusting phase and/or the measuring phase are triggered by therapy parameters.

In other words, if machine parameters and/or therapy parameters change, the adjusting phase and/or the measuring phase is started/triggered. For example, if the dialysis fluid flow is increased, the adjusting phase can be carried out with a reduction in the intensity of the radiation emitted by the radiation source, since the increase in the dialysis fluid flow results in a dilution of the dialysis fluid with regard to the concentration of substances usually excreted in the urine or light-absorbing substances.

In a further aspect of the device, the adjusting phase and the measuring phase are carried out at defined times of the extracorporeal blood treatment.

In other words, before the start of the extracorporeal blood treatment, it is determined at which times of the extracorporeal blood treatment the adjusting phase and the measuring phase are to be carried out. Preferably, more adjusting phases and measuring phases are carried out at the beginning of the extracorporeal blood treatment than at the end of the extracorporeal blood treatment. Further preferably, adjusting phases and measuring phases are only carried out at the beginning and at the end of the extracorporeal blood treatment.

By reducing the number of measuring cycles in particular, the service life of the radiation source can be extended and energy can be saved.

In a further aspect of the device, an opacity of the cuvette is determined by a change in the ratio between the intensity of the radiation detected at the measuring detection unit and the intensity of the radiation detected at the reference detection unit.

In other words, a current S1 is applied to the radiation source and the ratio r is calculated from the intensity of the detected radiation at the measuring detector M(S1) and the intensity of the radiation of the detected radiation at the reference detector R(S1) using the rule $$r = \frac{M(S1)}{R(S1)}$$

preferably in the regulation/control unit. This ratio r is stored and preferably compared with at least one other stored ratio r. If it is then determined that the ratio r has dropped, this indicates that the cuvette is cloudy. Preferably, a corresponding message is issued to the operator.

Furthermore, an average or median value is preferably formed from several stored ratios r, with which the currently determined ratio r is compared.

For example, the ratio r can be compared with the mean value of the previous five ratios r determined. Alternatively, the ratio r can be compared with the median value of the previous five ratios r determined.

In addition, a trend analysis of the ratio r may be carried out over a longer period of time. Such a trend analysis can be used to identify changes to the device or other components.

In a further aspect of the device, the current intensities and the duration with which the radiation source is subjected to the current intensities are stored and a prediction of the (remaining) service life of the radiation source is carried out using these stored values.

In other words, current intensities and/or therapy numbers and/or the cumulative measurement duration (the duration for which the radiation source was switched on) are stored and a prediction of the remaining service life of the radiation source is derived from this.

This allows an operator to request a replacement/spare part before the device fails so that the device can be replaced before it fails.

Optionally, the prediction may be output to the operator as a graphic. The ordering of a replacement may also optionally be recommended or carried out semi-automatically or fully automatically. Semi-automatic or fully automatic ordering is carried out, for example, via a procurement system connected to the device.

In a further aspect of the device, the radiation source does not emit radiation during the entire measuring phase. The radiation is preferably emitted at cyclical intervals. For example, the radiation source may be deactivated for five or more minutes during a measuring phase and then may be reactivated for a measuring period of a few seconds.

In a further aspect, the current intensity applied to the radiation source may be described by a monotonically decreasing function.

In a further aspect, the cuvette may be arranged between the radiation source and the measuring detection unit.

DETAILED DESCRIPTION

Figure 1:
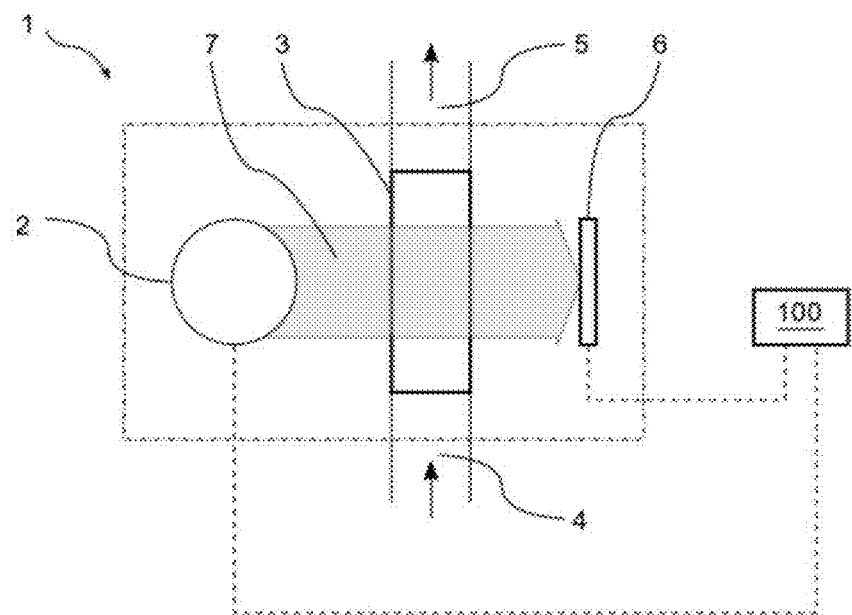
FIG. 1 is a representation of a device according to a first embodiment of the present invention.

Configuration examples of the present invention are described below on the basis of the associated Figures.
First Configuration Examples FIG. 1 shows a (measuring) device 1 according to the invention, which comprises a radiation source 2, in particular a light source, for substantially monochromatic electromagnetic radiation, a cuvette 3, in particular a tubular flow cell, with a dialysis fluid inlet 4 and a dialysis fluid outlet 5 as well as a detection unit 6, in particular a photodetector. The detection unit 6 is provided and configured to measure/detect the intensity of a radiation 7 emitted by the radiation source 2. The detection unit 6 is provided and configured in the device 1 so that it measures the intensity of the radiation 7 emitted/radiated by the radiation source 2 after it has passed the cuvette 3. The wavelength of the radiation 7 emitted by the radiation source 2 is in the ultraviolet range, for example at 280 nm or 254 nm. The intensity of the radiation 7 emitted by the radiation source 2 is regulated by the regulation/control unit 100. The regulation/control unit 100 also processes the signal from the detection unit 6.

Figure 2:
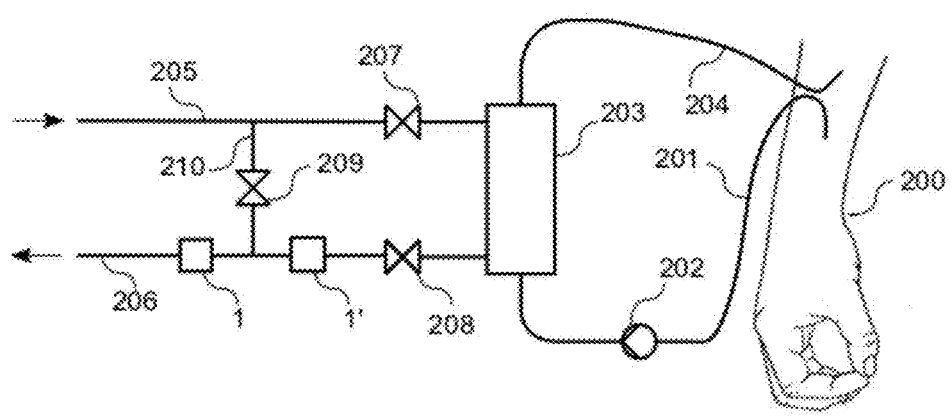
FIG. 2 is a representation illustrating the integration of a device according to the invention according to the first or a second embodiment into the treatment setup of the extracorporeal blood treatment.

FIG. 2 shows a treatment setup of an extracorporeal blood treatment. During an extracorporeal blood treatment, blood from a patient 200 is conveyed via an arterial line 201 to a dialyzer 203 using a conveyor unit 202, in particular a blood pump, where it is purified and returned to the patient 200 via a venous line 204. In the opposite direction to the blood flow, unused dialysis fluid flows from a line 205 into the dialyzer 203. The dialysis fluid absorbs (UV) radiation-absorbing substances usually excreted in the urine from the blood of the patient 200 by diffusion and convection and conducts these radiation-absorbing substances usually excreted in the urine through a further dialysis fluid line 206 in the direction of an outlet. A bypass line 210 allows the dialysis fluid to bypass the dialyzer 203 by opening a valve 209 and closing valves 207 and 208. Downstream of the dialyzer 203, in relation to the direction of flow of the dialysis fluid, the device 1 according to the invention is located in the dialysis fluid line 206. The device 1 may be located downstream (1 in FIG. 2) or upstream (1' in FIG. 2) of the point where the bypass line 210 opens into the dialysis fluid line 206 in the direction of flow of the dialysis fluid.

Through the substance exchange processes within the dialyzer 203, substances usually excreted in the urine pass from the blood into the dialysis fluid. Some of these substances absorb ultraviolet radiation/light, which can be detected by the device 1 according to the invention. The higher the concentration of radiation-absorbing substances usually excreted in the urine in the dialysis fluid, the lower the measured intensity of the radiation 7 at the detection unit 6.

In the course of extracorporeal blood treatment, the concentration of radiation-absorbing substances usually excreted in the urine gradually decreases both in the blood and in the spent dialysis fluid, whereby the intensity of the radiation 7 at the detection unit 6 increases if the intensity of the radiation 7 emitted by the radiation source 2 remains constant.

Figure 3:
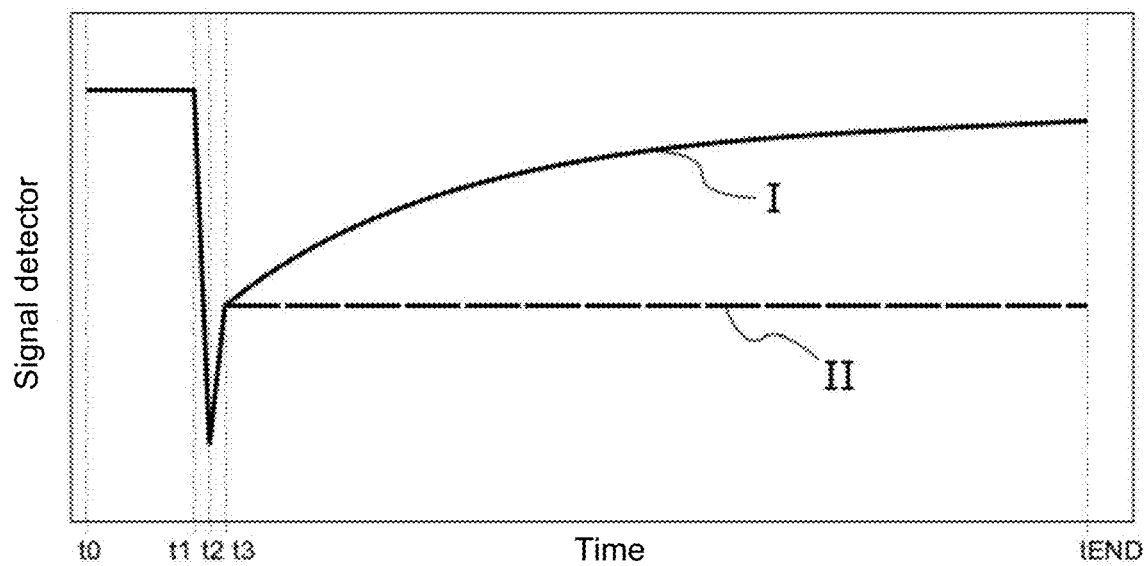
FIG. 3 is a diagram showing the signal/intensity of the radiation at a measuring detection unit of the first embodiment over the temporal course of the extracorporeal blood treatment.
Figure 4:
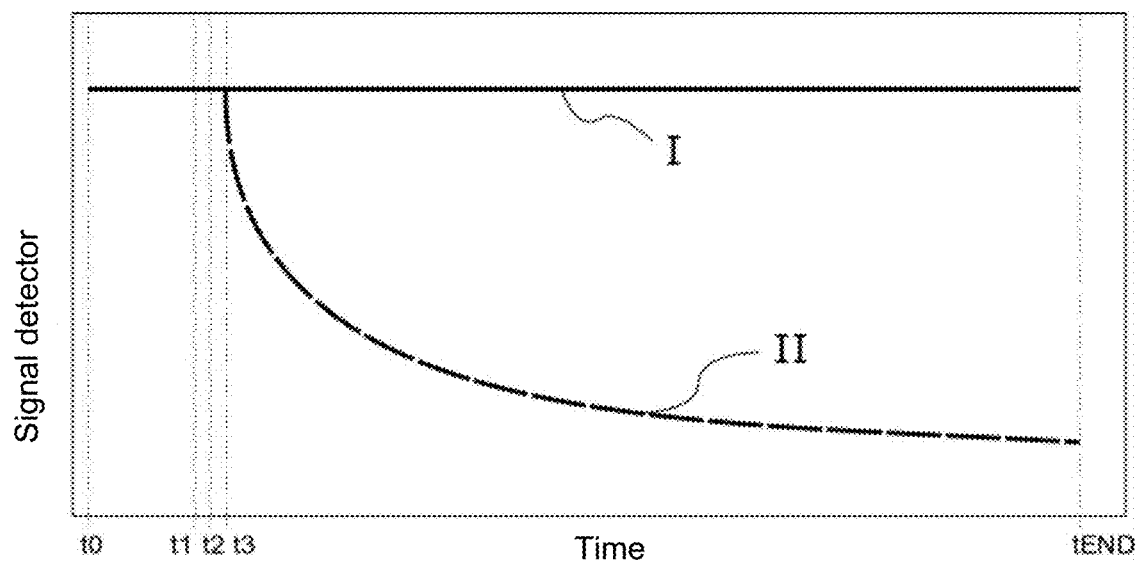
FIG. 4 is a diagram showing the current/the current intensity applied to the radiation source of the first embodiment over the temporal course of the extracorporeal blood treatment.

FIG. 3 schematically shows the signal curve at the detection unit 6 and FIG. 4 the associated current/the associated current intensity for operating the radiation source 2.

At time t0, the radiation source 2 is operated with a predefined, constantly high current. In the period t0 to t1, the dialysis machine is in bypass. The patient 200 is applied during this time, which means that the blood first begins to flow through the dialyzer 203 at a low blood flow rate and then at a blood flow rate that increases up to the target blood flow rate. Since the dialysis fluid flows past the dialyzer 203 while the dialysis machine is in the bypass, there are no radiation-absorbing substances usually excreted in the urine in the dialysis fluid. The intensity measured at the detection unit 6 is therefore also high, depending on the current applied to the radiation source. As soon as the target blood flow is reached, the bypass mode is deactivated and the actual dialysis/extracorporeal blood treatment begins.

During the bypass, there is a saturation of radiation-absorbing substances usually excreted in the urine on the dialysis fluid side of the dialyzer 203, which is limited by the closed valves 207 and 208. Shortly after the end of the bypass, the saturated dialysis fluid passes the device 1, resulting in a steep drop in the measuring signal/the detected intensity of the radiation at the detection unit 6 at a time t2. As soon as the concentration bolus has passed the device 1, the measuring signal/the detected intensity of the radiation 7 at the detection unit 6 rises again. A time t3 indicates the end of the measuring signal caused by the concentration bolus.

In FIG. 3 and FIG. 4, I denotes the signal that is measured at the detection unit 6 if the current intensity is kept constant to operate the radiation source 2.

According to the invention, however, it is not the current intensity that is kept constant, but the detected intensity of the radiation 7 at the detection unit 6 from time t3. This is done by adjusting the current intensity. Any conventional controller type can be used for this, preferably PI or PID controllers. The detected intensity of the radiation 7 at the detection unit 6 at time t3 is the reference input variable, the detected intensity of the radiation 7 at the detection unit 6 is the process variable and the current intensity is the controlled variable.

The signals according to the invention are labeled II in FIG. 3 and FIG. 4.

The current I with which the radiation source 2 is operated is now used to determine the Kt/V value:

$$\frac{Kt}{V} = \ln\left(\frac{I(t3)}{I(t)}\right)$$

Or $$sp\frac{Kt}{V} = -\ln\left(-0.008 \times t + \frac{I(t)}{I(t3)}\right) + \left(4 - 3.5 \times \frac{I(t)}{I(t3)}\right) \times \frac{UF}{W}$$

In the temporal course of the therapy/extracorporeal blood treatment, the concentration of radiation-absorbing substances usually excreted in the urine decreases in the spent dialysis fluid, whereby a lower current intensity is required to keep the detected intensity of the radiation 7 at the detection unit 6 constant.

By gradually lowering the current intensity, the radiation source 2 is subjected to less stress, which extends the service life of the radiation source 2.

The duration of the detected signal curve between t1 and t3 can be assumed to be known with a duration of 60 seconds to 90 seconds, depending on the dialysis fluid flow. Since t1 is known as the time of deactivation of the initial bypass, t3 is also known.

The time span t1 to t3 is very short compared to the remaining therapy duration/the duration of the remaining extracorporeal blood treatment. Preferably, the time span t1 to t3 is 0.5% of the total therapy duration.

It is known that the intensity of the radiation 7 emitted by the radiation source 2 depends on the temperature. Thus, the intensity of radiation 7 decreases for increasing temperatures at constant current. Common dialysis machines already have a temperature sensor at the dialysis fluid outlet. Although the dialysis fluid temperature is quite constant during the course of a therapy, this temperature sensor can be used to compensate for a possible temperature influence. In the following equation, the flow is compensated to a reference temperature value of 37° C., for example:

$$I_{37°\,C.} = I_T - \alpha \times (T - 37°\,C.)$$

where $I_{37°\,C.}$ is the current compensated to 37° C., $I_T$ is the current detected at the measured temperature T and $\alpha$ is a temperature coefficient.

Second Configuration Examples

Figure 5:
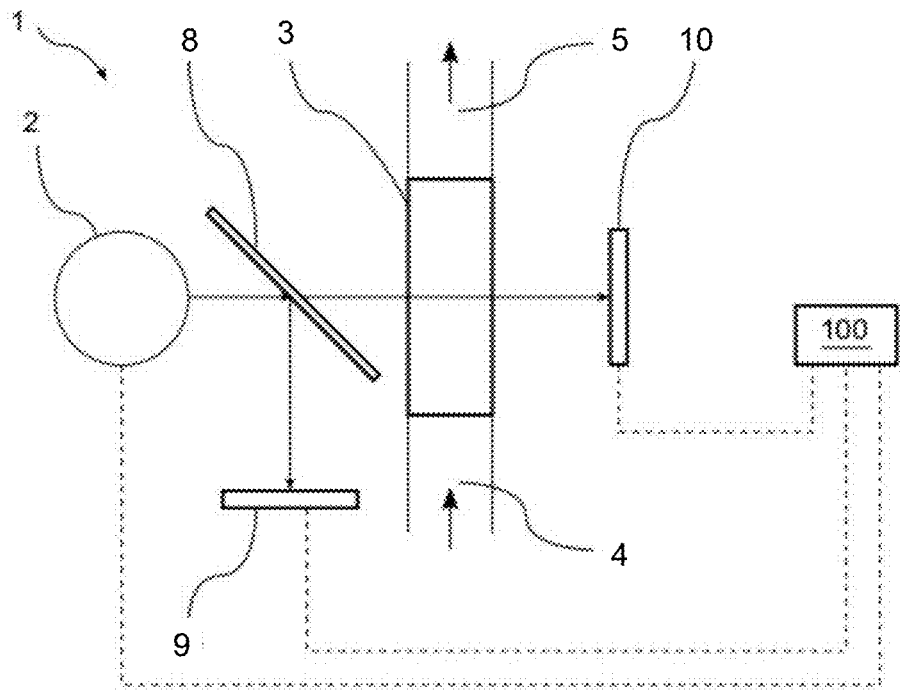
FIG. 5 is an illustration of a device according to a second embodiment of the present invention.

FIG. 5 shows a (measuring) device 1 according to the invention, which comprises a radiation source 2, in particular a light source, for substantially monochromatic electromagnetic radiation, a semi-transparent radiation divider 8, in particular a light divider, a cuvette 3, in particular a tubular flow cell, with dialysis fluid inlet 4 and dialysis fluid outlet 5 as well as a reference detection unit 9, in particular a reference photodetector, and a measuring detection unit 10, in particular a measuring photodetector. The reference detection unit 9 measures the intensity of the radiation, which is partially reflected by the radiation divider 8. The measuring detection unit 10 measures the intensity of the radiation that is emitted by the radiation source 2 and then passes through the cuvette 3. The wavelength of the emitted radiation is in the ultraviolet range, for example at 280 nm or 254 nm. The intensity of the emitted radiation is regulated by the regulation/control unit 100 by adjusting the current intensity. The regulation/control unit 100 also processes the signal from the reference detection unit 9 and the measuring detection unit 10.

The reference detection unit 9 compensates for possible fluctuations in the intensity of the radiation emitted by the radiation source 2. One possible cause of such intensity fluctuations is, for example, a change in temperature.

The radiation divider 8 can be omitted if the reference detection unit 9 is positioned in such a way that it also detects the radiation emitted by the radiation source 2 without the radiation passing through the cuvette 3 first.

FIG. 2 shows a treatment setup of an extracorporeal blood treatment. During an extracorporeal blood treatment, blood from a patient 200 is conveyed via an arterial line 201 to a dialyzer 203 using a conveyor unit 202, in particular a blood pump, where it is purified and returned to the patient 200 via a venous line 204. In the opposite direction to the blood flow, unused dialysis fluid flows from a line 205 into the dialyzer 203. The dialysis fluid absorbs (UV) radiation-absorbing substances usually excreted in the urine from the blood of the patient 200 by diffusion and convection and conducts these radiation-absorbing substances usually excreted in the urine through a further dialysis fluid line 206 in the direction of the outlet. Via a bypass line 210, the dialysis fluid can be diverted past the dialyzer 203 by opening a valve 209 and closing valves 207 and 208. Downstream of the dialyzer, in relation to the direction of flow of the dialysis fluid, the device 1 according to the invention is located in the dialysis fluid line 206. The device 1 is located downstream (1 in FIG. 2) or upstream (1' in FIG. 2) of the point where the bypass line 210 opens into the dialysis fluid line 206 in the direction of flow of the dialysis fluid.

Figure 6:
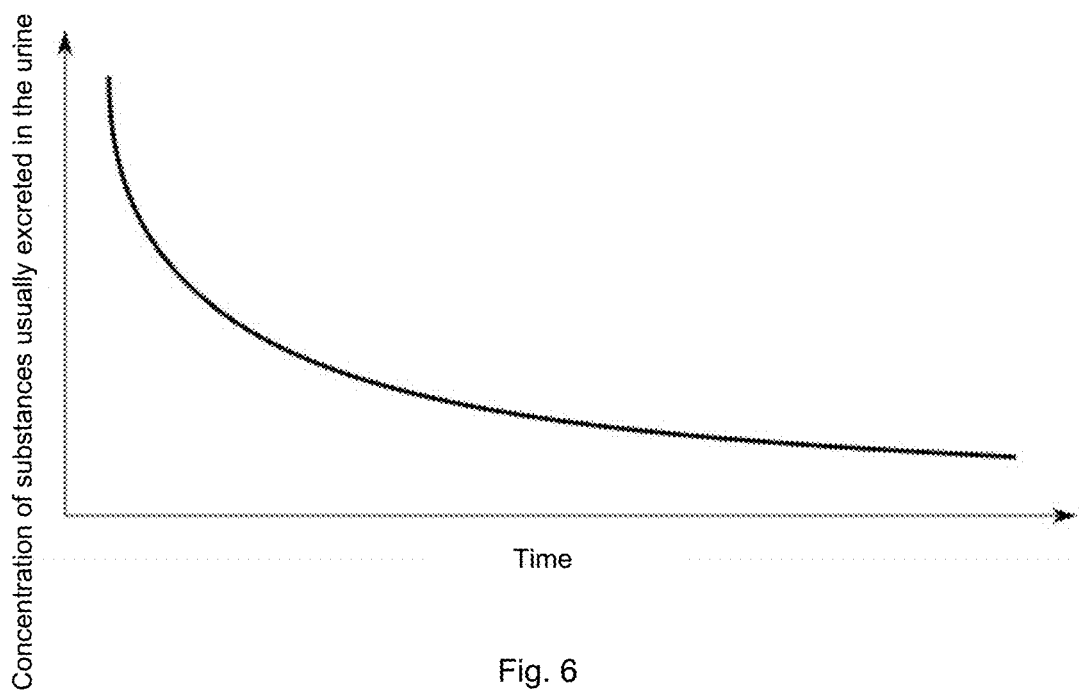
FIG. 6 is a diagram showing the concentration of substances usually excreted in the urine both in the blood and in the dialysis fluid over the temporal course of the extracorporeal blood treatment.

FIG. 6 shows that due to the mass transfer processes within the dialyzer 203 (UV) radiation-absorbing substances usually excreted in the urine pass from the blood into the dialysis fluid, whereby the concentration of radiation-absorbing substances usually excreted in the urine gradually decreases both in the blood and in the dialysis fluid in the temporal course of the extracorporeal blood treatment.

The following is shown that the decrease in concentration over time correlates with the absorbance/absorption rate or extinction in the dialysis fluid.

The following procedure describes how the absorbance or extinction, which is ultimately required to determine the Kt/V value, can be determined according to the invention.

1. Device Identification SI

In the first step, fresh, i.e. uncontaminated dialysis fluid flows through the cuvette 3. This is the case, for example, when the dialysis fluid side of the dialyzer is initially rinsed with dialysis fluid. This flushing is also known as priming. The regulation/control unit 100 sets a first current/a first current intensity S1 for operating the radiation source 2. Preferably, the current S1 is selected such that the resulting intensity of the radiation from the radiation source 2 is within the measuring range of the measuring detection unit 10.

Since the radiation divider 8 only reflects part of the emitted radiation in the direction of the reference detection unit 9, the intensity of the radiation measured at the reference detection unit 9 R(S1) at current S1 is lower than the intensity of the radiation measured at the measuring detection unit 10 M(S1). The values S1, R(S1) and M(S1) are stored.

In the second step of device identification, the current is reduced to the value S2:

$$S2 = S1 \times \alpha$$

with $\alpha < 1$, for example $\alpha = 0.75$. S2 and the resulting intensity values at the measuring detection unit 10 and at the reference detection unit 9 M(S2) and R(S2) are also stored.

Figure 7:
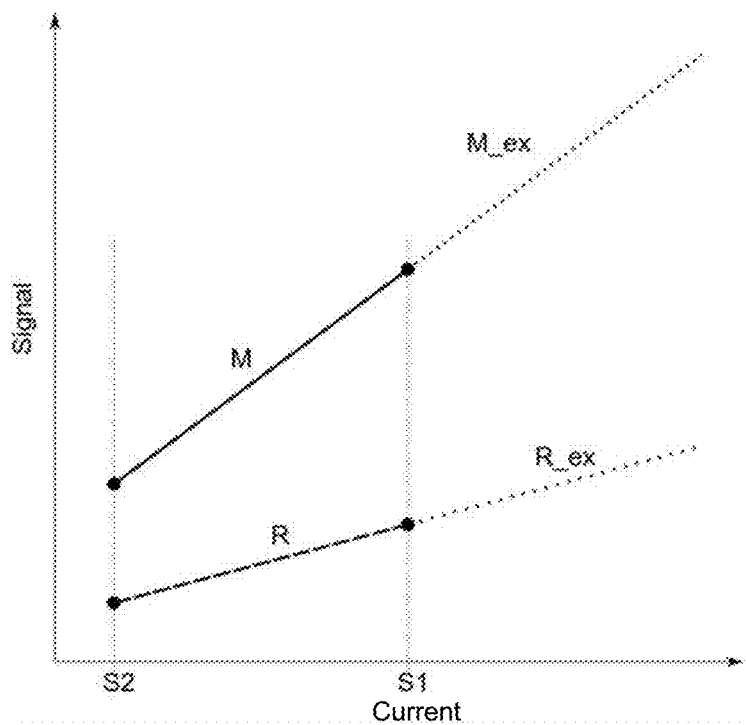
FIG. 7 is a diagram representing a device identification of the second embodiment, wherein the signal/intensity of the radiation at the measuring detection unit and at the reference detection unit is plotted against the current/current intensity.

As a linear relationship between current/current intensity and measured intensity values of the radiation can be assumed, two measuring points are sufficient for the next step. Alternatively, at least one further current value can be set and the corresponding intensities can be measured and stored at the reference detection unit 9 and at the measuring detection unit 10. Then, based on the values determined, the characteristic curves shown in FIG. 7 are created, which describe the intensity at the reference detection unit 9 and at the measuring detection unit 10 as a function of the current intensity:

$$M = a \times S + b$$

$$R = c \times S + d$$

Alternatively, it is conceivable to reduce the current (quasi-)continuously from the value S2 to a final value and to save all or some of the measured values in a look-up table.

It is also conceivable to use polynomials of a higher degree to describe the relationships between current and intensities at the reference detection unit 9 and at the measuring detection unit 10.

Alternatively, it is also possible to first set a low current and then increase it instead of reducing it.

2. First Adjusting Phase EP1

After the device 1 has been identified, the current value/the current intensity is adjusted in a first adjusting phase EP1 until a first target value MSoll1 is reached at the measuring detection unit 10. A P, PI or PID controller is used for this purpose, for example.

A value RSoll1 detected at the reference detection unit 9 is stored. Preferably, the value is stored by the regulation/ control unit 100. The value RSoll1 is then kept constant by the regulation/control unit 100 by adjusting the current intensity. For example, a P, PI or PID controller is used for this purpose.

3. First Measuring Phase MP1

Figure 8:
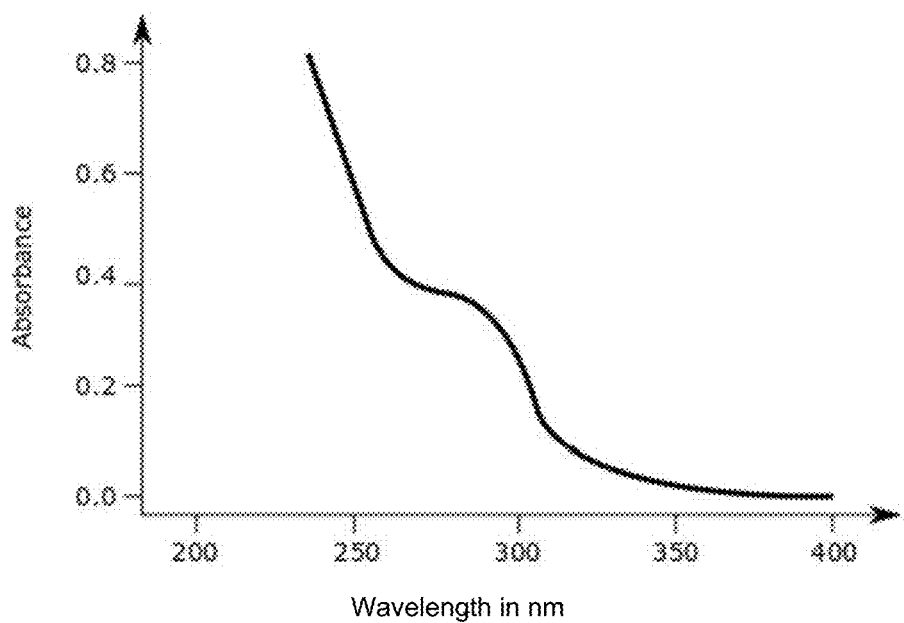
FIG. 8 is a diagram that schematically shows a typical absorption spectrum of a dialysis fluid. The absorption of the dialysis fluid is plotted against the wavelength in nm.

As soon as the device 1 is adjusted, the patient's blood 200 can be passed through the dialyzer 203. Through diffusion and/or convection, substances usually excreted in the urine reach the dialysis fluid side. Some of these substances absorb ultraviolet radiation. FIG. 8 schematically shows a typical absorption spectrum of a dialysis fluid. In order to avoid measurements on edges, a radiation source 2 is selected according to the invention, which emits radiation with a wavelength of 280 nm, for example. The absorbance in the first measuring phase A1 is determined according to:

$$A1 = \log\left(\frac{MSoll1}{M}\right)$$

MSoll1 is the target value from the first adjusting phase and M is the value M measured at the measuring detection unit 10.

In particular at the beginning of a treatment, the concentration of radiation-absorbing substances usually excreted in the urine in the used dialysis fluid is quite high, which means that the measured value M at the measuring detection unit 10 may be low. This may lead to incorrect measurement results because, for example, it is no longer possible to distinguish between noise and the true measured value. For this reason, the invention alternatively provides for a value Mex to be used for the first target value MSoll1 which is above the measuring range of the measuring detection unit 10. As shown in FIG. 7, this can be done by extrapolating the values recorded during the device identification phase. The target value can assume any value as long as the corresponding value at the reference detection unit 9 Rex is within the measuring range of the reference detection unit 9 in order to continue to ensure successful control.

This procedure makes it possible to measure the absorbance at higher concentrations of radiation-absorbing substances, which is equivalent to increasing the linear measuring range of device 1.

4. Second Adjusting Phase EP2

As mentioned above, the concentration of radiation-absorbing substances usually excreted in the urine in the dialysis fluid decreases in the course of the extracorporeal blood treatment, as a result of which the measured intensity of the radiation at the measuring detection unit 10 tends to increase if the radiation emitted by the radiation source 2 has a constant intensity. According to the present invention, the intensity or the current intensity or the target value at the measuring detection unit 10 or the target value at the reference detection unit 9 is therefore reduced at least once. In the simplest case, this is done by applying the characteristic curves determined in the device identification phase:

$$RSoll2 = \frac{c}{a} \times (MSoll2 - b) + d$$

If the device 1 is behind the point where the bypass line 210 opens into the dialysis fluid line 206 in the flow direction of the dialysis fluid, the device 1 can alternatively be briefly switched to bypass mode to readjust the device 1. Since pure dialysis fluid flows through the device 1 shortly after the start of the bypass, RSoll2 can be determined analogously to the first adjusting phase.

5. Second Measuring Phase MP2

In the second measuring phase, the absorbance is determined in the same way as in the first measuring phase:

$$A2 = \log\left(\frac{MSoll2}{M}\right)$$

With further reductions, the adjusting and measuring phases are repeated accordingly. The duration of the adjusting phases is significantly shorter than that of the measuring phases.

During the adjusting phase, no absorbance values are determined that would be included in the determination of dialysis efficiency (e.g. in the Kt/V).

Figure 9:
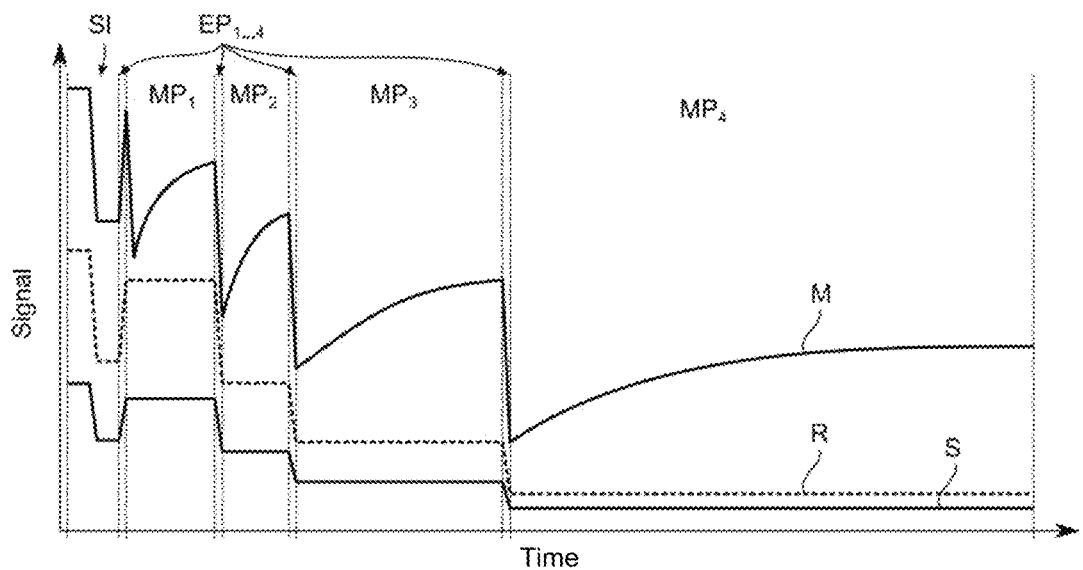
FIG. 9 is a diagram which schematically shows a course of the signal of the measuring detection unit, the signal of the reference detection unit and the current/the current intensity of a second embodiment over the temporal course of the extracorporeal blood treatment.

FIG. 9 shows an example of the course of the signals of the measuring detection unit 10, the reference detection unit 9 and the current in the course of a therapy/an extracorporeal blood treatment with four reductions of the intensity or the current or the target values. In the respective measuring phases, the signal at the reference detection unit 9 is kept constant by adjusting the current.

The number of reductions and the respective duration of the measuring phases is variable and can be preset, for example.

Since the approximately exponential decay of the concentration of radiation-absorbing substances usually excreted in the urine in the blood and in the dialysis fluid shown in FIG. 6 means that a faster reduction in absorbance can be expected at the beginning of therapy, it is advisable to reduce the intensity more at the beginning than at the end of therapy.

Alternatively, new adjusting and measuring phases are started if the parameters of the dialysis machine or the treatment change. If, for example, the dialysis fluid flow is increased from the standard 500 ml/min to 800 ml/min, the intensity of the radiation emitted by the radiation source 2 can also be reduced, as the increase in dialysis fluid flow causes a dilution of the dialysis fluid with regard to the concentration of radiation-absorbing substances usually excreted in the urine. The same applies to the extracorporeal blood flow. If, on the other hand, an increase in the concentration of radiation-absorbing substances usually excreted in the urine is to be expected (for example in the case of a decrease in dialysis fluid flow or an increase in blood flow), the intensity of the radiation emitted by the radiation source 2 may even be increased.

The radiation source 2 does not necessarily have to emit radiation continuously. During a measuring phase, for example, it can also be switched off for a period of five or several minutes and then switched on again for a measuring period of a few seconds. This change can take place cyclically.

The present invention provides for storing current values and the number of therapies and/or the cumulative measurement time and deriving a prediction about the remaining service life of the radiation source 2. Cumulative measurement time is to be understood as the total duration for which radiation source 2 was switched on.

The current value is, for example, the current that is required in the first adjusting phase to reach the target value MSoll1 at the measuring detection unit 10. The prediction can be used to request a replacement part in good time so that the device 1 can be replaced before the radiation source 2 fails.

Figure 10:
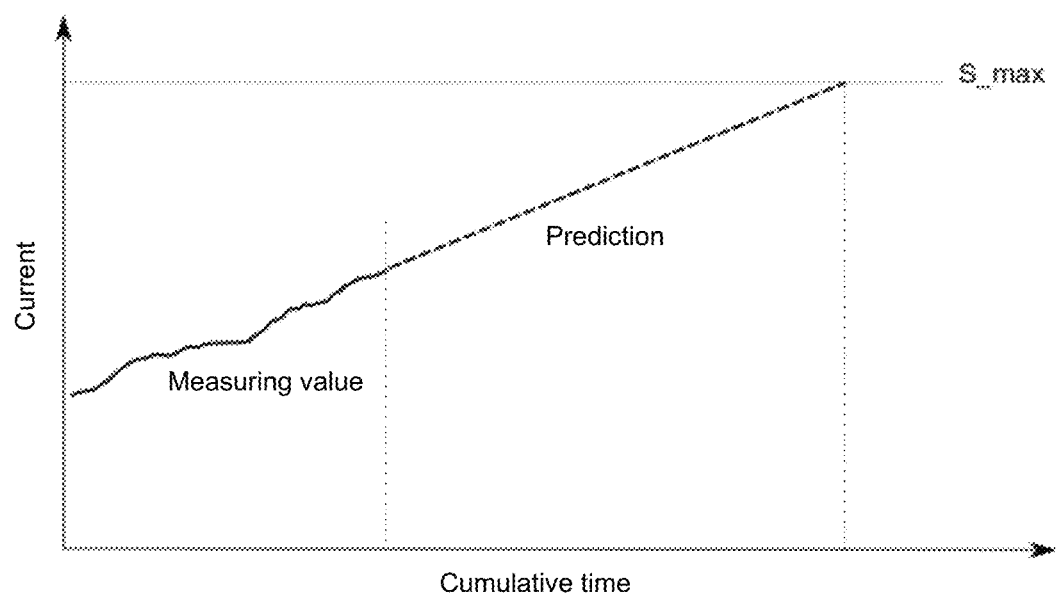
FIG. 10 is an example of a diagram that is displayed to an operator of the dialysis machine and shows the prediction of the service life of the radiation source.

The graphic in FIG. 10 can be made available to the operator, in particular the medical staff and/or the technical staff and/or the manufacturer of the measuring device. This is preferably done by displaying it on a screen of the dialysis device or by transmitting it to a data management system. An order for the spare part can either be recommended or carried out semi-automatically or fully automatically if the connection to a corresponding procurement system is available, for example.

Alternatively, the device is configured such that the radiation source 2 can be replaced individually.

In order to delay a possible failure of the device, the number of measuring cycles is reduced according to the invention.

Figure 11:
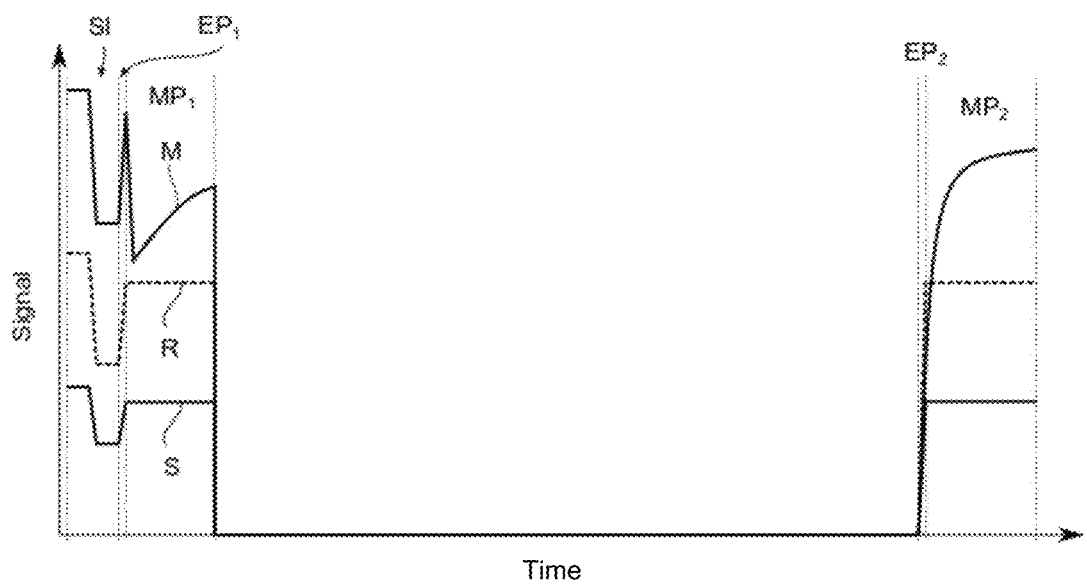
FIG. 11 is a diagram which schematically shows a course of the signal of the measuring detection unit, of the signal of the reference detection unit and the current/the current intensity of a second embodiment over the temporal course of the extracorporeal blood treatment, wherein an adjusting phase and a measuring phase are present only at the beginning and at the end of the temporal course of the therapy.

FIG. 11 shows the extreme case with only two measuring phases at the beginning and end of a therapy, as at least the initial and final absorbance values must be given to determine the Kt/V value.

In addition to reducing the number of measurement cycles, the intensity of the radiation emitted by the radiation source 2 may also be reduced, as described above.

Another optional feature of the invention is to evaluate the ratio r between the value of the measuring detection unit 10 and the value of the reference detection unit 9 during device identification in order to detect possible opacities of the cuvette 3. This can be done when applying a current S1 with the rule:

$$r = \frac{M(S1)}{R(S1)}$$

The ratio r is stored over several device identification phases. If it turns out that the ratio r in a device identification phase is significantly lower than, for example, the mean value or median of the previous five device identifications, this indicates that the cuvette 3 is cloudy, which may have been caused by the machine not being disinfected and descaled after the last treatment, or not being disinfected and descaled sufficiently. A corresponding message is preferably displayed on the screen of the dialysis machine and disinfection is carried out by an operator. Alternatively, an acoustic signal is emitted or a warning lamp lights up.

A trend analysis over a longer period of time, for example since the device was first commissioned, can also be carried out to detect possible gradual changes in the components of the device. If the ratio r changes over a longer period of time and disinfection or descaling of the dialysis machine does not cause a change in r, this may indicate that the response behavior of the measuring detection unit 10 and/or the reference detection unit 9 is deteriorating. Here too, it is conceivable that an early request for spare parts is triggered.

Since the intensity of the radiation emitted by the radiation source 2, which is measured by the measuring detection unit 10 and the reference detection unit 9, is temperature-dependent, the measured values or the current can be temperature-compensated. The temperature measured by a temperature sensor on the dialysis fluid side downstream of the dialyzer 203 or by a temperature sensor integrated in the device 1 is used for this purpose. Compensation to a temperature of 37° C. is recommended, as this is the usual temperature of the dialysis fluid.

The invention claimed is:

1. A device for determining a dialysis efficiency/dialysis dose of an extracorporeal blood treatment with a radiation source, a cuvette, at least one detection unit and a regulation/control unit, wherein
    the radiation source is intended and configured to emit a radiation, the intensity of which is controlled/regulated by adjusting a current strength to which the radiation source is subjected,
    the cuvette is provided with a dialysis fluid inlet and a dialysis fluid outlet and is intended and configured to be penetrated by the radiation emitted by the radiation source,
    the detection unit is provided and adapted to detect, as a measurement detection unit, the intensity of the radiation after it has passed the cuvette,
    the regulation/control unit determines the dialysis efficiency/dialysis dose from the intensity of the radiation detected by the detection unit,
    wherein
    the regulation/control unit is connected to the radiation source and the detection unit and is provided and configured to reduce the intensity of the emitted radiation by adjusting the current strength over the time course of the extracorporeal blood treatment at least once, based on a decrease in a concentration of urinary substances in the dialysis fluid.

2. The device according to claim 1, wherein the regulation/control unit is provided and configured to control the radiation source in such a way that the intensity of the radiation detected by the detection unit remains constant over the time course of the extracorporeal blood treatment.

3. The device according to claim 2, wherein the current strength applied to the radiation source is evaluated/used for determining the dialysis efficiency/dialysis dose.

4. The device according to claim 3, wherein the dialysis efficiency/dialysis dose is the Kt/V value, where K describes the clearance, t the therapy duration and V the patient-specific distribution volume of urea in the body, and the regulation/control unit is provided and configured to determine the dialysis efficiency/dialysis dose via the rule Kt/V=ln(I(t3)/I(t)), where I describes the current strength, t3 a fixed point in time and t the therapy duration.

5. The device according to claim 3, wherein the dialysis efficiency/dialysis dose is the Kt/V value, where K describes the clearance, t the therapy duration and V the patient-specific distribution volume of urea in the body, and the regulation/control unit is provided and configured to determine the dialysis efficiency/dialysis dose via the rule Kt/V=−ln(−0.008*t+(I(t)/I(t3))+(4−3.5*(I(t)/I(t3))*UF/W, where I describes the current strength, t3 describes a fixed point in time, t describes the therapy duration, UF describes the ultrafiltration volume and W describes the weight of the patient.

6. The device according to claim 3, wherein the current strength is normalized to a reference temperature value.

7. The device according to claim 1, wherein the device comprises a further detection unit provided and configured to detect the intensity of the radiation emitted from the radiation source as a reference detection unit, wherein the course of therapy comprises at least one regulation phase and at least one measuring phase, wherein the regulation/control unit reduces the intensity of the emitted radiation over the time course of the extracorporeal blood treatment at least once in the regulation phase and the regulation/control unit controls the radiation source by adjusting the current strength in such a way that the intensity of the radiation detected by the reference detection unit remains constant during the measuring phase and the intensity of the radiation is evaluated at the measuring detection unit for determining the dialysis efficiency/dialysis dose during the measuring phase.

8. The device according to claim 7, wherein the regulation phase and/or the measuring phase are triggered by therapy parameters.

9. The device according to claim 7, wherein the regulation phase and the measuring phase are performed at defined times of the extracorporeal blood treatment.

10. The device according to claim 7, wherein an opacity of the cuvette is determined by a ratio change between the intensity of the radiation detected at the measuring detection unit and the intensity of the radiation detected at the reference detection unit.

11. The device according to claim 1, wherein the current strengths and the duration with which the radiation source is subjected to the current strengths are stored and a prediction of the lifetime of the radiation source is carried out via these stored values.

12. The device according to claim 1, wherein the cuvette is arranged between the radiation source and the measuring detection unit.

* * * * *